| United States Patent [19] | [11] Patent Number: 4,753,800 |
|---|---|
| Mozda | [45] Date of Patent: Jun. 28, 1988 |

[54] MEDICAMENT ADSORBATES AND THEIR PREPARATION

[75] Inventor: Ronald F. Mozda, Edison, N.J.

[73] Assignee: Warner-Lambert Company, Morris Plains, N.J.

[21] Appl. No.: 784,280

[22] Filed: Oct. 4, 1985

[51] Int. Cl.$^4$ .............................. A61J 3/10; A61K 9/00
[52] U.S. Cl. .................................. 424/440; 424/441
[58] Field of Search .............................. 424/440, 441

[56] References Cited

U.S. PATENT DOCUMENTS

| Re. 27,697 | 12/1966 | Barry et al. | |
|---|---|---|---|
| 3,140,978 | 7/1964 | Zentner | 167/55 |
| 3,248,290 | 4/1966 | Zentner | 167/55 |
| 3,337,402 | 8/1967 | Zentner | 424/155 |
| 3,432,593 | 3/1969 | Shepard | 424/20 |
| 3,567,819 | 3/1971 | Idson et al. | 424/155 X |
| 3,636,200 | 1/1972 | Zentner | 424/155 X |
| 4,029,797 | 6/1977 | Bianculli | 424/260 |

*Primary Examiner*—Michael R. Lusignan
*Attorney, Agent, or Firm*—Charles A. Gaglia, Jr.; Gary M. Nath

[57] ABSTRACT

A medicament adsorbate and process for making same. The medicament adsorbate comprises a complex magnesium aluminum silicate having sorbed therein an edible wax and a medicament drug.

23 Claims, No Drawings

MEDICAMENT ADSORBATES AND THEIR PREPARATION

FIELD OF THE INVENTION

This invention relates to a medicament adsorbate composition and in particular to a medicament adsorbate which contains a complex magnesium aluminum silicate having sorbed thereon a homogenous mixture of an edible wax and a medicament drug.

DESCRIPTION OF THE PRIOR ART

The use of complex magnesium aluminum silicate has been taught in the literature as a method to render bitter drug principles tasteless in liquid, tablet and chewable dosage forms which become readily bioavailable when the adsorbate reaches the low pH acid media of the stomach.

U.S. Pat. No. 3,337,402 to Zentner discloses the formation of a sedative composition using 7-chloro-1-methyl-5-phenyl-3H-1,4-benzodiazepin-2(1H)-one adsorbed on a complex magnesium aluminum silicate. Zentner notes that when the drug is first dissolved in a lower molecular weight monohydroxy aliphatic alcohol or in an aqueous alcohol mixture and then mixed with a complex magnesium aluminum silicate, the bitter taste and anesthetizing effect on the tongue associated with the drug is reduced or eliminated. Zentner also discloses that the adsorbate may be mixed with other ingredients to form lozenges, tablets, candies, capsules and suspensions.

U.S. Pat. No. 3,567,819 to Idson, et al discloses the formation of a decongestant composition using phenylpropanolamine hydrochloride adsorbed on a complex magnesium aluminum silicate. The objectionable taste of phenylpropanolamine hydrochloride is reduced or eliminated when the drug is first placed in solution and then mixed with complex magnesium aluminum silicate to form an adsorbate. The adsorbate is then dried and used to prepare a chewable multilayered tablet.

SUMMARY OF THE INVENTION

A procedure for preparing a good tasting medicament adsorbate which may contain up to about 50% by weight medicament compound has been unexpectedly discovered.

This has been achieved by incorporating the medicament in a melted edible wax and then admixing a complex magnesium aluminum silicate with the melted wax-medicament mixture to form a mass which when cooled and ground is a good tasting medicament adsorbate.

DETAILED DESCRIPTION

In particular, it has been found that a good tasting medicament adsorbate is produced from admixing about 1 to about 25% by weight of a medicament drug with about 8 to about 50% by weight of a melted edible wax to form a dispersion. The dispersion is then further admixed with about 25 to about 91% by weight of a complex magnesium aluminum silicate until it is sorbed therein to form a homogenous mixture.

While the invention is not to be limited to theoretical considerations, it is believed that when the medicament drug is added to the melted wax, the medicament either dissolves in the wax and/or melts and is dispersed throughout the wax by mixing. The complex magnesium aluminum silicate is then added to the wax-medicament solution or co-melt. The medicament and wax are then sorbed into the complex magnesium aluminum silicate. The wax acting as both a solvent or carrier for the medicament and as sealent after the medicament has been sorbed into the complex magnesium aluminum silicate.

The wax-medicament solution or co-melt may alternatively be added to the complex magnesium aluminum silicate with mixing. This may be accomplished by pouring, spraying or related techniques known in the art.

It is believed that this sorbing of the hot wax-medicament solution or co-melt into the complex magnesium aluminum silicate renders the medicament not available for organoleptic taste prior to passage into the digestive tract and subsequent desorption by the gastric juice. This taste masking sorption effect is not found in the wax medicament mixture alone. The taste masking sorption effect of this invention is superior to the taste masking found when a medicament drug is adsorbed merely from aqueous, organic or mixed solvents onto a complex magnesium aluminum silicate.

In the practice of the present invention, the complex magnesium aluminum silicate is a standard article of commerce. The typical average chemical analysis of complex magnesium aluminum silicate, conventionally expressed as oxides, maybe represented as follows:

|  | Percent by Weight |
| --- | --- |
| Silicon dioxide | 55 to 70 |
| Magnesium oxide | 2.9 to 25 |
| Aluminum oxide | 2.0 to 17 |
| Ferric oxide | 0.4 to 1.8 |
| Calcium oxide | 1.1 to 2.4 |
| Sodium oxide | 1.0 to 3.8 |
| Potassium oxide | 0.2 to 1.9 |
| Ignition Loss | 5.5 to 12.6 |

In a preferred embodiment of the invention, the complex magnesium aluminum silicate has the following typical chemical analysis:

|  | Percent by Weight |
| --- | --- |
| Silicon dioxide | 56 to 59 |
| Magnesium oxide | 21 to 24 |
| Aluminum oxide | 2.0 to 4.0 |
| Ferric oxide | 0.4 to 0.6 |
| Calcium oxide | 1.1 to 1.5 |
| Sodium oxide | 2.5 to 3.5 |
| Potassium oxide | 0.5 to 1.0 |
| Ignition Loss | 5.5 to 12.6 |

The complex magnesium aluminum silicate of this invention is present in an amount from about 25 to about 91 percent by weight of the final adsorbate complex. In a preferred embodiment, the complex magnesium aluminum silicate is present in an amount of about 40 to about 80 percent by weight of the final adsorbate complex and most preferably from about 50 to about 75 percent.

It has been found that the particle size of the complex magnesium aluminum silicate is not critical in preparing the adsorbates of this invention. While not essential the average particle size of the complex magnesium aluminum silicate may range from about 10 to about 150 microns. Such products have been found suitable to sorb sufficient quantities of the wax-drug complex to prepare acceptable product.

The term edible wax used herein refers to a low-melting organic mixture or compound of high molecular weight, solid at room temperature and generally similar in composition to fats and oils except that it contains no glycerides. Some are hydrocarbons; others are esters of fatty acids and alcohols. Waxes are thermoplastic, but since they are not high polymers, they are not considered in the family of plastics. Common properties of waxes are water repellency; smooth texture; nontoxicity; freedom from objectionable odor and color.

Waxes are combustible, have good dielectric properties, are soluble in most organic solvents and insoluble in water. The major types of wax are as follows:

I. Natural
 1. Animal: beeswax, spermaceti, lanolin, shellac wax.
 2. Vegetable: carnauba, candelilla, bayberry, sugarcane.
 3. Mineral
   (a) Fossil or earth waxes: ozocerite, ceresin.
   (b) Petroleum waxes: paraffin, microcrystalline.
II. Synthetic
 1. Ethylenic polymers and polyol ether-esters polyethylene glycol sorbitol
 2. Hydrocarbon type via Fischer-Tropsch synthesis having the formula $CnH_{(2n+2)}$.

In a preferred embodiment, the wax is selected from the group consisting of carnauba wax, candelilla wax, paraffin, castor wax, beeswax, stearic acid, stearyl alcohol, cetyl alcohol, esters of fatty alcohols and mixtures thereof. Most preferably the wax is selected from the group consisting of carnauba wax, candelilla wax, paraffin, castor wax, beeswax and mixtures thereof.

In a preferred embodiment, the edible wax is present in an amount from about 8 to about 50 percent by weight of the final adsorbate complex and most preferably present from about 10 to about 35 percent.

The medicament drugs used herein may be selected from a wide variety of drugs and their acid addition salts. Both organic and inorganic salts may be used provided the drug maintains its medicament value and is soluble in or will co-melt with the hot edible wax. Exemplary acid salts include hydrochloride, hydrobromide, orthophosphate, benzoate, maleate, tartrate, succinate, citrate, salicylate, sulfate and acetate.

The weight percent of the drug or its acid addition salt thereof based on the weight of the adsorbate is preferably from about 1% to about 25%, and most preferably about 5% to about 18%, which amounts will vary depending upon the therapeutic dosage permitted.

The medicament drug may be selected from a wide range of unpleasant tasting therapeutic agents and mixtures of therapeutic agents. Nonlimiting illustrative categories and specific examples include:
(a) Analgesics, such as acetaminophen, ibuprofen, and salicylamide;
(b) Antiasmatics, such as metaproterenol, and theophylline;
(c) Antitussives, such as dextromethorphan, dextromethorphan hydrobromide, noscapine, carbetapentane citrate, and chlophedianol hydrochloride;
(d) Antihistamines, such as chlorpheniramine maleate, phenindamine tartrate, pyrilamine maleate, doxylamine succinate, phenyltoloxamine citrate, diphenhydramine hydrochloride, promethazine, and triprolidine;
(e) Antinauseant, such as dimenhydrinate, and meclizine;
(f) Decongestants, such as phenylephrine hydrochloride, phenylpropanolamine hydrochloride, pseudoephedrine hydrochloride, ephedrine;
(g) Various alkaloids, such as codeine phosphate, codeine sulfate and morphine;
(h) Laxatives and vitamins, such as phenolphthalein, danthron, and bisocadyl;
(i) Anti-cholesterolemic and anti-lipid agents such as gemfibrozil;
(j) Appetite suppressants such as phenylpropanolamine hydrochloride, and caffeine;
(k) Central nervous system stimulants such as nicotine;
(l) Expectorants such as guaifenesin; and
(m) Anti-inflammatory agents such as isoxicam, and meclophenamic acid.

Medicaments may be used alone or in combination within the ranges specified above to form the adsorbate.

In a preferred embodiment the medicament is selected from the group consisting of dextromethorphan, dextromethorphan hydrobromide, pseudoephedrine, pseudoephedrine hydrochloride, guaifenesin and mixtures thereof.

The medicament adsorbate of the invention is prepared by melting an edible wax to form a liquid, admixing a medicament drug with the melted wax to form a co-melt or solution, admixing complex magnesium aluminum silicate with the wax-drug mixture to sorb the wax-drug mixture onto the silicate and to prepare a particulate mass having a homogenous consistency. The wax-medicament solution or co-melt may alternatively be added to the complex magnesium aluminum silicate with mixing. This may be accomplished by pouring, spraying or related techniques known in the art. Once formed the particulate mass is cooled and recovered.

To form a wax-medicament drug solution, the edible waxes of the present invention are heated to a temperature above their melting point to form a liquid but less than their decomposition point. A solution is formed as a wax soluble medicament drug is added to the liquid wax and dispersed with mixing.

The edible wax is preferably heated from about 90° to about 130° C. to form the liquid wax.

To form a wax medicament drug co-melt, the edible waxes of the present invention are heated to a temperature above their melting point to form a liquid but less than their decomposition point. For example, carnauba wax melts at 82° to 85.5° C. and can be heated to about 200° C. without causing thermal degradation. A co-melt is formed when the melting point of a nonwax soluble medicament drug is less than the temperature of the hot edible wax so that when the medicament drug is added to the hot edible wax the medicament drug will melt. Upon mixing, the co-melt will then form, a dispersion.

The medicament adsorbate of the invention can be prepared by melting from about 8 to about 50% by weight of the total composition of an edible wax to form a liquid, admixing the medicament drug in an amount from about 1 to about 25% by weight of the total composition with the liquified wax to form a solution or co-melt. Admixing about 25 to about 91% by weight of the total composition of a complex magnesium aluminum silicate with the wax-medicament drug mixture and sorbing the wax-medicament drug mixture onto the complex magnesium aluminum silicate to prepare a particulate mass having a homogenous consistency. Once formed, the particulate mass is cooled and recovered.

The medicament adsorbate once prepared may be stored for future use or formulated with conventional additives, that is pharmaceutically acceptable carriers, to prepare medicated compositions which offer a variety of textures to suit particular applications. Such compositions may be in the form of a lozenge, tablet, toffee, nougat, chewy candy, chewing gum, and so forth. The pharmaceutically acceptable carriers may be prepared from a wide range of materials. Without being limited thereto, such materials include diluents, binders and adhesives, lubricants, disintegrants, colorants, flavorings, sweeteners and miscellaneous materials such as buffers and adsorbents in order to prepare a particular medicated composition. The preparation of confectionary and chewing gum products is well known and does not constitute an essential aspect of this invention.

As used herein, the term confectionery material means a product containing a bulking agent selected from a wide variety of materials such as sugar and in the case of sugarless bulking agents sugar alcohols such as sorbitol and mannitol. Confectionery material may include such exeplary substances as lozenges, tablets, toffee, nougat, chewy candy and so forth. In general, the bulking agent will comprise from about 5 to about 99% and preferably 20 to about 95% by weight of the medicated confectionery product.

Lozenges are flavored medicated dosage forms intended to be sucked and held in the mouth. They may be in the form of various shapes, the most common being flat, circular, octagonal and biconvex forms. The lozenge bases are generally in two forms, hard, boiled candy lozenges and compressed tablet lozenges.

The hard boiled candy lozenges are prepared from a mixture of sugar and other carbohydrates that are kept in an amorphous or glassy condition. This form can be considered a solid syrup of sugars generally having from 0.5 to about 1.5% moisture. Such materials normally contain up to about 92% corn syrup, up to about 70% sugar and from 0.1% to about 5.0% water. The syrup component generally is prepared from corn syrups high in dextrose, but may include other materials. Further ingredients such as flavorings, sweeteners, acidulents, colorants and so forth may also be added.

Boiled candy lozenges may also be prepared from nonfermentable sugars such as sorbital, mannitol, and hydrogenated corn syrup. A typical hydrogenated corn syrup is lycasin. The candy lozenges may contain up to about 95% sorbitol, a mixture of sorbitol and mannitol at a ratio of about 9.5 to 0.5 up to about 7.5 to 2.5 and hydrogenated corn syrup up to about 55% of the syrup component.

In contrast, compressed tablet lozenges contain particular materials and are formed into structures under pressure. They generally contain sugars in amounts up to 95% and typical tablet excipients such as binders and lubricants as well as flavors, colorants and so forth.

The lozenges may be made of soft confectionary materials such as those contained in nougat. These materials contain two primary components, namely a high boiling syrup such as corn syrup or the like, and a relatively light textured frappe, generally prepared from gelatin, egg albumen, milk proteins such as casein, and vegetable proteins such as soy protein, and the like. The frappe is generally relatively light, and may, for example, range in density from about 0.5 to about 0.7 g/cc.

By comparison, the high boiling syrup, or "bob syrup," is relatively viscous and possesses a higher density, and frequently contains a substantial amount of sugar. Conventionally, the final nougat composition is prepared by the addition of the "bob syrup" to the frappe under agitation, to form the basic nougat mixture. Further ingredients such as flavorings, oils, additional sugar and the like may be added thereafter also under agitation. A general discussion of the composition and preparation of nougat confections may be found in B. W. Minifie, CHOCOLATE, COCOA AND CONFECTIONERY: *Science and Technology*, 2nd edition, AVI Publishing Co., Inc., Westport, Conn., (1980), at pages 424–425.

Pharmaceutical tablets of this invention may also be in the form of chewable forms. This form is particularly advantageous because of convenience and patient acceptance. To achieve acceptable stability and quality as well as good taste and mouth feel several considerations are important, namely amount of active substance per tablet, flavor, compressibility and organoleptic properties of the drug.

The preparation of chewable medicated candy is by procedures similar to those used to make soft confectionary products. This procedure generally involves the formation of a boiled sugar-corn syrup blend to which is added a frappe mixture. The boiled sugar-corn syrup blend may be prepared from sugar and corn syrup blended in parts by weight ratio of about 90 to 10 to about 10 to 90. This blend is heated to temperatures above 121° C. to remove water and to form a molten mass. The frappe is generally prepared from gelatin, egg albumen, milk proteins such as casein, and vegetable proteins such as soy protein, and the like which are added to a gelatin solution and rapidly mixed at ambient temperature to form an aerated sponge like mass. The frappe is then added to the molten candy base and mixed until homogenous at temperatures between 65° C. and 121° C.

The medicament adsorbate can then be added as the temperature of the mix is lowered to about 65° to about 93° C. whereupon additional ingredients are added such as flavors, and colorants. The formulation is further cooled and formed to pieces of desired dimensions.

A general discussion of the lozenge and chewable tablet forms of confectionary may be found in H. A. Lieberman and L. Lachman, *Pharmaceutical Dosage Forms:* Tablets Volume 1, Marcel Dekker, Inc., New York, N.Y. at pages 289 to 466 which disclosure is incorporated herein by reference.

As used herein, the term chewing gum product means a product containing a chewing gum formulation. In general, the chewing gum formulation will comprise from about 5 to about 99% and preferably 20 to about 95% by weight of the medicated chewing gum product.

With regard to a chewing gum formulation, such formulations contain a gum base and various additives, such as sweeteners and flavors. The gum base employed will vary greatly depending on various factors such as the type of base used, consistency desired and other components used to make the final product. In general, amounts of about 5% to about 45% by weight of the final chewing gum composition are acceptable for use in chewing gum compositions with preferred amounts of about 15% to about 25% by weight. The gum base may be any water-insoluble gum base well known in the art. Illustrative examples of suitable polymers in gum bases include both natural and synthetic elastomers and rubbers. For example, those polymers which are suitable in gum bases, include, without limitation, substances of vegetable origin such as chicle, jelutong, gutta percha and crown gum. Synthetic elastomers such as butadiene-styrene copolymers, isobutylene-isoprene copolymers, polyethylene, polyisobutylene and polyvinylacetate and mixtures thereof, are particularly useful.

The gum base composition may contain elastomer solvents to aid in softening the elastomer component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, penta-erythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of alpha-pinene and beta-pinene; terpene resins including polyterpene and mixtures thereof. The solvent may be employed in an amount ranging from about 10% to about 75% and preferably about 45% to about 70% by weight to the gum base.

A variety of traditional ingredients such as plasticizers or softeners such as lanolin, stearic acid, sodium stearate, potassium stearate, glyceryl triacetate, glycerine and the like as well as natural and synthetic waxes, petroleum waxes, such as 35 polyurethane waxes, paraffin waxes and microcrystalline waxes may also be incorporated into the gum base to obtain a variety of desirable textures and consistency properties. These individual additional materials are generally employed in amounts of up to about 30% by weight and preferably in amounts from about 3% to about 20% by weight of the final gum base composition.

The chewing gum composition may additionally include the conventional additives of flavoring agents, coloring agents such as titanium dioxide, emulsifiers such as lecithin and glyceryl monostearate; and additional fillers such as aluminum hydroxide, alumina, aluminum silicates, calcium carbonate, and talc and combinations thereof. These fillers may also be used in the gum base in various amounts. Preferably the amount of fillers when used will vary from about 4% to about 30% by weight of the final chewing gum.

In the instance where auxiliary sweeteners are utilized, the present invention contemplates the inclusion of those sweeteners well known in the art, including both natural and artificial sweeteners. Thus, additional sweeteners may be chosen from the following non-limiting list:

A. Water-soluble sweetening agents such as monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol and mixtures thereof.

B. Water-soluble artificial sweeteners such as the soluble saccharin salts, ie., sodium, or calcium saccharin salts, cyclamate salts, acesulfame-K and the like, and the free acid form of saccharin.

C. Dipeptide based sweeteners such as L-aspartyl-L-phenylalanine methyl ester and materials described in U.S. Pat. No. 3,492,131 and the like.

In general, the amount of sweetener will vary with the desired amount of sweeteners selected for a particular chewing gum. This amount will normally be 0.001% to about 90% by weight when using an easily extractable sweetener. The water-soluble sweeteners described in category A above, are preferably used in amounts of about 25% to about 75% by weight, and most preferably from bout 50% to about 65% by weight of the final chewing gum composition. In contrast, the artificial sweeteners described in categories B and C are used in amounts of about 0.005% to about 5.0% and most preferably about 0.05% to about 2.5% by weight of the final chewing gum composition. These amounts are ordinarily necessary to achieve a desired level of sweetness independent from the flavor level achieved from flavor oils. While water may be added, independently, with dry sweeteners, it will generally be added as part of a corn syrup or corn syrup mixture.

Suitable flavorings include both natural and artificial flavors, and mints such as peppermint, menthol, artificial vanilla, cinnamon, various fruit flavors, both individual and mixed, and the like are contemplated. The flavorings are generally utilized in amounts that will vary depending upon the individual flavor, and may, for example, range in amounts of about 0.5% to about 3% by weight of the final composition.

The colorants useful in the present invention, include the pigments such as titanium dioxide, that may be incorporated in amounts of up to about 1% by weight, and preferably up to about 6% by weight. Also, the colorants may include other dies suitable for food, drug and cosmetic applications, and known as F.D. & C. dyes and the like. The materials acceptable for the foregoing spectrum of use are preferably water-soluble. Illustrative examples include the indigo dye, known as F.D. & C. Blue No. 2, which is the disodium salt of 5,5-indigotindisulfonic acid. Similarly, the dye known as F.D. & C. Green No. 1, comprises a triphenylmethane dye and is the monosodium salt of 4-[4-Nethyl-p-sulfobenzylamino)diphenylmethylene]-[1-(N-ethyl-N-p-sulfoniumbenzyl)-$2,5$-cyclohexadienimine]. A full recitation of all F.D. & C. and D. & C. colorants and their corresponding chemical structures may be found in the Kirk-Othmer Encyclopedia of Chemical Technology, in Volume 5, at pages 857–884, which text is accordingly incorporated herein by reference.

Suitable oils and fats that are usable would include partially hydrogenated vegetable or animal fats, such as coconut oil, palm kernel oil, beef tallow, lard, and the like. These ingredients are generally utilized in amounts with respect to the comestible product of up to about 7.0% by weight, and preferably up to about 3.5% by weight of the final product.

It is generally believed that as the required amount of active substance per structure gets smaller and/or less bad tasting, the task at arriving at an acceptable formulation becomes easier due to the greater number of formulations available. Alternatively, extremely bad-tasting and/or high-dose drugs are difficult to formulate into medicament/chewable tablets. The medicament adsorbates of this invention overcome these difficulties.

The quantity of adsorbate used may vary widely depending upon the particular medicament drug dosage. Amounts of medicament of about 1.0 to about 400 mg per medicated dosage are usable dependant upon the particular medicament. Naturally amounts of medicament adsorbate used will vary depending on the therapeutic dosage required and the amount of medicament sorbed on the substrate. Illustrative examples are described below.

The usual dosage of dextromethorphan hydrobromide is between 10 and 30 mg per tablet. Incorporation of the adsorbate into, for example, a candy base is not difficult. It is compatible with most flavors and is stable over a wide pH range. The dextromethorphan HBr when added as the medicament adsorbate avoids its bitter taste and flavoring difficulty.

The usual dosage of d-phenylpropanolamine hydrochloride is about 12.5 to 25 mg per tablet. The usual dosage of quaifenesin is 100 to 400 mg per tablet. The usual dosage of pseudoephedrine hydrochloride is 15 to 60 mg per tablet. The usual dosage range of chlorpheniramine maleate is 2 to 4 mg and lends itself easily to incorporation into a candy base. Naturally, the exact amount used will vary with the particular application and drug. These formulations are not difficult to flavor because the adsorbates formed with these compounds substantially eliminate medicament after-taste.

The medicament adsorbate is generally present with the pharmaceutically acceptable carrier in an amount of from about 1% to about 60% by weight of the final composition. The exact amount will be dependent upon the particular medicament and dosage required.

The present invention is further illustrated by the following examples. All parts and percentages in the examples and throughout the specification and claims are by total weight of the medicament adsorbate unless otherwise indicated.

EXAMPLE 1

(Inventive Run 1)

This Example demonstrates a method for preparing a quaifenesin adsorbate according to the process of the invention.

To 310 grams of melted carnauba wax held at about 90° to about 95° C. is mixed 160 grams of guaifenesin until a uniform mixture is obtained. To the guaifenesin-wax mixture, 530 grams of complex magnesium aluminum silicate having the following typical chemical analysis is added with mixing:

| | Percent by Weight |
|---|---|
| Silicon dioxide | 56 to 59 |
| Magnesium oxide | 21 to 24 |
| Aluminum oxide | 2.0 to 4.0 |
| Ferric oxide | 0.4 to 0.6 |
| Calcium oxide | 1.1 to 1.5 |
| Sodium oxide | 2.5 to 3.5 |
| Potassium oxide | 0.5 to 1.0 |
| Ignition Loss | 5.5 to 12.6 |

The mixing is continued for about 5 minutes at a mix temperature between 75° to 80° C. The particulate mass is allowed to cool. The resulting solid is then milled to produce a free flowing particulate material having a particle size of about 100 microns.

An organoleptic evaluation test was performed by a three person panel on the product to determine the presence or absence of bitterness associated with the product. The instant product did not exhibit objectable bitterness or off taste.

EXAMPLE 2

(Inventive Run 2)

This Example demonstrates as method for preparing a dextromethorphan hydrobromide adsorbate according to a process of the invention.

To 310 grams of melted carnauba wax held at about 90° to about 95° C. is mixed 50 grams of dextromethorphan hydrobromide until a uniform mixture is obtained. To the dextromethorphan wax mixture, 640 kilograms of complex magnesium aluminum silicate having the following typical chemical analysis is added with mixing:

| | Percent by Weight |
|---|---|
| Silicon dioxide | 56 to 59 |
| Magnesium oxide | 21 to 24 |
| Aluminum oxide | 2.0 to 4.0 |
| Ferric oxide | 0.4 to 0.6 |
| Calcium oxide | 1.1 to 1.5 |
| Sodium oxide | 2.5 to 3.5 |
| Potassium oxide | 0.5 to 1.0 |
| Ignition Loss | 5.5 to 12.6 |

The mixing is continued for about 5 minutes at a mix temperature between 75° to 80° C. The mass is allowed to cool. The resulting solid is then milled to produce a free flowing particulate material having a particle size of about 100 microns.

An organoleptic evaluation test was performed by a three person panel on the product to determine the presence or absence of bitterness. The instant product did not exhibit objectable bitterness or off taste when tested.

EXAMPLE 3

(Inventive Run 3)

This Example demonstrates a method for preparing a guaifenesin adsorbate according to a process of the invention.

To 310 grams of melted candelilla wax held at about 90° to about 95° C. is mixed 160 grams of guaifenesin until a uniform mixture is obtained. To the guaifenesin-wax mixture, 530 grams of complex magnesium aluminum silicate having the following typical chemical analysis is added with mixing:

| | Percent by Weight |
|---|---|
| Silicon dioxide | 56 to 59 |
| Magnesium oxide | 21 to 24 |
| Aluminum oxide | 2.0 to 4.0 |
| Ferric oxide | 0.4 to 0.6 |
| Calcium oxide | 1.1 to 1.5 |
| Sodium oxide | 2.5 to 3.5 |
| Potassium oxide | 0.5 to 1.0 |
| Ignition Loss | 5.5 to 12.6 |

The mixing is contained for about 5 minutes at a mix temperature between 75° to 80° C. The mass is allowed to cool. The resulting solid is then milled to produce a free flowing particulate material having a particle size of about 100 microns.

An organoleptic evaluation test was performed by a three person panel on the product to determine the presence or absence of bitterness. The instant product did not exhibit objectable bitterness or off taste.

EXAMPLE 4

(Comparative Run A)

This Example demonstrates a guaifenesin adsorbate prepared by the procedure of Example 1 except that magnesium trisilicate is employed instead of the complex magensium aluminum silicate.

To 310 grams of melted carnauba wax held at about 90° to about 95° C. is mixed 160 grams of guaifenesin until a uniform mixture is obtained. To the guaifenesin-wax mixture, 530 grams of magnesium trisilicate is added with mixing. The mixing is contained for about 5 minutes at a mix temperature between 75° to 80° C. The mass is allowed to cool. The resulting solid is then milled to produce a free flowing particulate material having a particle size of about 100 microns.

An organoleptic evaluation test was performed by a three person panel on the product to determine the presence or absence of bitterness. The instant product exhibited a bitter unacceptable taste.

EXAMPLE 5

(Inventive Run 4)

This Example demonstrates a method for preparing a cold/sinus/asthma tablet formulation using an adsorbate prepared according to a process of the invention with pseudoephedrine HCl.

The adsorbate may be prepared as follows: To 200 grams of melted wax is mixed 100 grams of pseudoephedrine until a uniform dispersion is obtained. To the pseudoephedrine-wax dispersion, 700 grams of complex magnesium aluminum silicate is added with mixing.

The following ingredients are mixed in the order indicated:

| No. | Ingredients | Mg/Tablet |
| --- | --- | --- |
| 1. | Chlorpheniramine maleate | 4.0 |
| 2. | Pseudoephedrine HCl-10% adsorbate (60.0 mg drug/tablet) | 600.0 |
| 3. | Microcrystalline cellulose | 37.3 |
| 4. | Lactose | 113.0 |
| 5. | Modified cellulose gum | 2.2 |
| 6. | Fumed silica | 1.1 |
| 7 | Stearic acid | 1.3 |
| 8. | Magnesium stearate | 1.1 |
|  |  | 760.0 |

PROCEDURE

Pass #2, #3 and #4 through a 40 mesh screen. Mix in a V-blender for 3 minutes. Pass #1, #5, #6, #7 and #8 through a #40 mesh screen. Add to the mixture in the V-blender and mix for 15 minutes. Compress powders using 16/32" flat faced punches to a hardness of 5–7 S.C. units.

EXAMPLE 6

(Inventive Run 5)

This Example demonstrates a method for preparing a antihistamine tablet formulation using an adsorbate prepared according to a process of the invention from pyrilamine maleate.

The adsorbate may be prepared as follows: To 200 grams of melted wax is mixed 100 grams of pyrilamine maleate until a uniform dispersion is obtained. To the pyrilamine maleate-wax dispersion, 700 grams of complex magnesium aluminum silicate is added with mixing.

The following ingredients are mixed in the order indicated:

| No. | Ingredients | Mg/Tablet |
| --- | --- | --- |
| 1. | Pyrilamine maleate adsorbate - 10% adsorbate (25 mg drug/tablet) | 250.0 |
| 2. | Microcrystalline cellulose | 34.0 |
| 3. | Lactose | 136.8 |
| 4. | Modified cellulose gum | 2.0 |
| 5. | Fumed silica | 0.7 |

-continued

| No. | Ingredients | Mg/Tablet |
| --- | --- | --- |
| 6. | Stearic acid | 0.5 |
| 7. | Magnesium stearate | 1.0 |
|  |  | 425.0 |

PROCEDURE

Screen #1, #2, #3, #4, #5, #6 and #7 through 30 mesh sieve. Mix in a V-blender for 15 minutes. Tablet using 7/16" flat faced punches to a hardness of 5–7 S.C. units.

EXAMPLE 7

Comparative Runs B and C

This Example compares the taste properties derived from combining guaifenesin with wax alone and complex magnesium aluminum silicate alone to the taste properties of the adsorbate prepared in Example 1.

Taste masking only occurs in the adsorbate prepared in Example 1.

| Run | Adsorbate Taste |
| --- | --- |
| Inventive 1 | Good |
| Comparative B (guaifenesin and wax) | Bitter |
| Comparative C (guaifenesin and complex magnesium aluminum silicate) | Bitter |

Comparative B is 16% by weight guiafensin and is prepared by adding 59 grams of guiafenesin to 310 grams of melted carnauba wax held at about 90° to about 95° C. with mixing until a uniform mixture is obtained. The mixture is cooled to form a solid mass. The resulting solid is then milled to produce a particulate material having a particle size of about 100 microns.

Comparative C is prepared by dissolving 160 grams guaifenesin in water heated to 80° to 90° C. to form a solution. The guaifenesin solution is then added to 840 grams of complex magnesium aluminum silicate with mixing the resulting mixture is oven dried at 70° to 80° C. to form a powder containing 16% by weight guaifenesin having a typical particle size of about 100 microns.

EXAMPLE 8

Inventive Run 6

This Example demonstrates a method for preparing a chewable cough tablet formulation using an adsorbate prepared with guaifenesin prepared by the process of Example 1. The ingredients are mixed in the order indicated:

| No. | Ingredients | Mg/tablet |
| --- | --- | --- |
| 1. | Guaifenesin - 16% adsorbate (100 mg drug/tablet) | 625.0 |
| 2. | Candy base | 3630.5 |
| 3. | Frappe | 130.0 |
| 4. | Crystal sorbitol | 123.0 |
| 5. | Vegetable fat (palm kernel oil) | 265.0 |
| 6. | Sugar, granulated | 138.0 |
| 7. | Flavor | 88.5 |
|  |  | 5000.0 |

PROCEDURE

132° C. candy base is cooled in a kettle to a temperature of 110° to 115° C. The frappe and sorbitol crystals are then mixed into the base to form a uniform mass. Mixing is continued until the mass is cooled to 73° to 80° C. To the uniform mass is added with mixing the vegetable fat, color, and medicament adsorbate. The sugar and flavor are combined with mixing and added to the previous blend. Mixing is continued until a homogeneous mass is obtained. The product is removed from the kettle, cooled and then formed into 5 gram pieces. The tablet when chewed did not exhibit objectionable medicinal aftertaste due to the bitterness of the guaifenesin.

EXAMPLE 9

Inventive Run 1

This Example demonstrates the therapeutic availability of guaifenesin from the inventive adsorbate of Example 1.

In vitro dissolution test of the inventive product has been conducted. The results indicate the percent guaifenesin in solution at 60 minutes for three runs to be 85.1, 84.4 and 84.7. The average amount of guaifenesin in solution at 60 minutes is 84.7 percent.

Dissolution procedure:

Using the apparatus and procedure described in The National Formulary XIV, page 985, run a dissolution of the adsorbate as follows:

Place 625 mg of adsorbate sample into each of three bottles and to each bottle add 80 ml of 0.1N hydrochloric acid previously warmed to 37° C.±0.5° C. Cap the bottles tightly, and place them in the clamps on the shaft of the apparatus. Rotate the bottles at 40±2 rpm in the water bath maintained at 37° C.±0.5° C.

At the end of 1 hour, stop the rotor. Individually filter the contents of each bottle through a #1 Whatman filter paper with the aid of vacuum. Analyze the undissolved residue for guaifenessin content.

The invention being thus described, it will be obvious that the same may be varied in many ways. Such variations are not to be regarded as a departure from the spirit and scope of the invention and all such modifications are intended to be included within the scope of the following claims.

I claim:

1. A medicament adsorbate which comprises an effective amount of a complex magnesium aluminum silicate, having sorbed therein a dispersion of an effective amount of a medicament drug in an effective amount of an edible wax.

2. The medicament adsorbate of claim 1 wherein the complex magnesium aluminum silicate is present in an amount of about 25 to about 91% by weight, the edible wax is present in an amount of about 8 to about 50% by weight, and the medicament drug is present in an amount of about 1 to about 50% by weight of the medicament adsorbate.

3. The medicament adsorbate of claim 1 wherein the medicament drug is selected from the group consisting of analgesics, antiasmatics, antitussives, antihistamines, antinauseants, decongestants, expectorants, alkaloids, laxatives, vitamins, anti-cholesterolemic and anti-lipid agents, appetite suppressants, anti-inflammatory agents and mixtures thereof.

4. The medicament adsorbate of claim 1 wherein the medicament drug is the expectorant guaifenesin.

5. The medicament adsorbate of claim 1 wherein the medicament drug is selected from the group of antitussive materials consisting of dextromethorphan, dextromethorphan hydrobromide, noscapine, carbetapentane citrate, chlophedianol hydrochloride and mixtures thereof.

6. The medicament adsorbate of claim 1 wherein the medicament drug is selected from the group of analgesics consisting of acetaminophen, ibuprofen, salicylamide and mixtures thereof.

7. The medicament adsorbate of claim 1 wherein the medicament drug is selected from the group of antiasmatics consisting of metaproterenol, theophylline and mixtures thereof.

8. The medicament adsorbate of claim 1 wherein the medicament drug is selected from the group of antihistamines, consisting of chlorpheniramine maleate, phenindamine tartrate, pyrilamine maleate, doxylamine succinate, phenyltoloxamine citrate, diphenhydramine hydrochloride, promethazine, triprolidine and mixtures thereof.

9. The medicament adsorbate of claim 1, wherein the medicament drug is selected from the group of decongestants, consisting of phenylephrine hydrochloride, phenylpropanolamine hydrochloride, pseudophedrine hydrochloride, ephedrine and mixtures thereof.

10. The medicament adsorbate of claim 1 wherein the medicament drug is selected from the group of alkaloids consisting of codeine phosphate, codeine sulfate, morphine and mixtures thereof.

11. The medicament adsorbate of claim 1 wherein the medicament drug is selected from the group of laxatives consisting of phenolphthalein, danthron, bisocadyl and mixtures thereof.

12. The medicament adsorbate of claim 1 wherein the medicament drug is the anti-cholesterolemic and anti-lipid agent gemfibrozil.

13. The medicament adsorbate of claim 1 wherein the medicament drug is selected from the group of anti-inflammatory agents consisting of ioxicam meclophenamic acid and mixtures thereof.

14. The medicament adsorbate of claim 1 wherein the medicament drug is selected from the group of antinauseants consisting of dimenhydrinate, meclizine and mixtures thereof.

15. The medicament adsorbate of claim 1 wherein the medicament drug is selected from the group of appetite suppressants consisting of phenylpropanolamine hydrochloride, caffeine and mixtures thereof.

16. The medicament adsorbate of claim 1 wherein the medicament drug is the central nervous system stimulant nicotine.

17. The medicament adsorbate of claim 1 wherein the edible wax is selected from the group consisting of carnauba wax, candelilla wax, paraffin, castor wax, bees wax, stearic acid, stearyl alcohol, cetyl alcohol, esters of fatty alcohols and mixtures thereof.

18. A process for preparing a medicament adsorbate which comprises melting an effective amount of an edible wax to form a liquid, admixing an effective amount of a medicament drug selected from the group consisting of analgesics, antiasthmatics, antitussives, antihistamines, antinauseants, decongestants, expectorants, alkaloids, laxatives, vitamins, anti-cholesterolemic and anti-lipid agents, appetite suppressants, anti-inflammatory agents and mixtures thereof with the melted wax, admixing an effective amount of complex magnesium aluminum silicate with the melted wax-drug mixture to sorb the wax-drug mixture onto the complex magnesium aluminum silicate, cooling the particulate mass and recovering the medicament adsorbate product.

19. The process of claim 18 which comprises: employing about 8 to about 50% by weight edible wax, about 1 to about 50% by weight medicament drug and about 25 to about 91% by weight complex magnesium aluminum silicate.

20. A medicated composition which comprises a pharmaceutically acceptable carrier and from about 1% to about 60% by weight of the final composition of a medicament adsorbate containing about 25 to about 91% by weight of the adsorbate of a complex magnesium aluminum silicate having sorbed therein, from about 1% to about 50% by weight of the adsorbate of a medicament drug selected from the group consisting of analgesics, antiasmatics, antitussives, antihistamines, decongestants, expectorants, alkaloids, laxatives, vitamins, anti-cholesterolemic and anti-lipid agents, appetite suppressants, anti-inflammatory agents and mixtures thereof and from about 8% to about 50% by weight of the adsorbate of an edible wax selected from a group consisting of carnauba wax, candelilla wax, paraffin, castor wax, beeswax, stearic acid, stearyl alcohol, cetyl alcohol, esters of fatty alcohols and mixtures thereof.

21. The medicated composition of claim 9 wherein the pharmaceutically acceptable carrier is selected from a group consisting of a lozenge, a tablet, toffee, nougat, chewy candy and chewing gum.

22. A medicated confectionary product comprising:
a bulking agent of up to about 99%;
a therapeutically effective amount of a medicament adsorbate comprising an effective amount of a complex magnesium aluminum silicate having sorbed therein a dispersion of an effective amount of a medicated drug in an effective amount of an edible wax,
said medicament adsorbate being admixed in the confectionary product,
all percents herein are by weight of the medicated confectionary product.

23. A medicated chewing gum product containing a therapeutically effective amount of medicament drug which comprises
a chewing gum composition in an amount up to about 99% comprising:
a gum base; and
a sweetener;
a therapeutically effective amount of a medicament adsorbate comprising an effective amount of a complex magnesium aluminum silicate having sorbed thereon a dispersion of an effective amount of a medicated drug in an effective amount of an edible wax,
said medicament adsorbate being admixed in the chewing gum composition,
all percents herein are by weight of the medicated chewing gum product.

* * * * *

UNITED STATES PATENT AND TRADEMARK OFFICE
CERTIFICATE OF CORRECTION

PATENT NO. : 4,753,800

DATED : June 28, 1988

INVENTOR(S) : Ronald F. Mozda

It is certified that error appears in the above-identified patent and that said Letters Patent is hereby corrected as shown below:

In Claim 3, line 3 thereof, "antiasmatics" should read --antiasthmatics--.

In Claim 7, lines 2 and 3 thereof, "antiasmatics" should read --antiasthmatics--.

In Claim 13, line 3 thereof, "ioxicam" should read --isoxicam--.

In Claim 20, line 9 thereof, "antiasmatics" should read --antiasthmatics--.

Signed and Sealed this

Twenty-second Day of November, 1988

*Attest:*

DONALD J. QUIGG

*Attesting Officer*   *Commissioner of Patents and Trademarks*